United States Patent
Andrade

(10) Patent No.: US 12,290,244 B2
(45) Date of Patent: May 6, 2025

(54) METHOD FOR RECONDITIONING AN ENDOSCOPE IN A RECONDITIONING APPARATUS, AND RECONDITIONING APPARATUS

(71) Applicant: OLYMPUS WINTER & IBE GMBH, Hamburg (DE)

(72) Inventor: Jan Batista Andrade, Hamburg (DE)

(73) Assignee: Olympus Winter & Ibe GmbH, Hamburg (DE)

( * ) Notice: Subject to any disclaimer, the term of this patent is extended or adjusted under 35 U.S.C. 154(b) by 308 days.

(21) Appl. No.: 18/126,075

(22) Filed: Mar. 24, 2023

(65) Prior Publication Data

US 2023/0225603 A1 Jul. 20, 2023

Related U.S. Application Data

(62) Division of application No. 16/628,334, filed as application No. PCT/EP2018/064670 on Jun. 4, 2018, now Pat. No. 11,638,518.

(30) Foreign Application Priority Data

Jul. 3, 2017 (DE) .......................... 102017114816.7

(51) Int. Cl.
*A61B 1/00* (2006.01)
*A61B 1/12* (2006.01)
(Continued)

(52) U.S. Cl.
CPC .......... *A61B 1/125* (2013.01); *A61B 1/00057* (2013.01); *A61B 1/00059* (2013.01);
(Continued)

(58) Field of Classification Search
CPC . A61B 1/125; A61B 1/00057; A61B 1/00059; A61B 1/123; B08B 9/0321; B08B 13/00; B08B 2209/027
See application file for complete search history.

(56) References Cited

U.S. PATENT DOCUMENTS 5,494,530 A 2/1996 Graf
6,408,682 B2 6/2002 Greszler
(Continued)

FOREIGN PATENT DOCUMENTS

DE 10 2013 223 375 A1 5/2015
DE 102016200037 B3 * 6/2017
(Continued)

OTHER PUBLICATIONS

DE102016200037 translation (Year: 2017).*
(Continued)

*Primary Examiner* — Michael E Barr
*Assistant Examiner* — Lauren G Orta
(74) *Attorney, Agent, or Firm* — Scully, Scott, Murphy & Presser, P.C.

(57) ABSTRACT

A reconditioning apparatus for an endoscope including a controller configured to: supply an interior of the endoscope with a fluid at a predefined pressure; supply one or more channels of the endoscope and an exterior of the endoscope with a rinsing liquid to carry out a reconditioning process using the rinsing liquid; concurrently with the supplying of the rinsing liquid, determine a temperature and a pressure in the interior of the endoscope during the reconditioning process; and when the determined pressure decreases lower than a predetermined pressure: identify the endoscope as not defective, when the decrease in the determined pressure is preceded by a corresponding decrease in the determined temperature, and identify the endoscope as defective, when
(Continued)

the decrease in the determined pressure is not preceded by a corresponding decrease in the determined temperature.

20 Claims, 3 Drawing Sheets

(51) Int. Cl.
*B08B 9/032* (2006.01)
*B08B 13/00* (2006.01)

(52) U.S. Cl.
CPC .......... *A61B 1/123* (2013.01); *B08B 9/0321* (2013.01); *B08B 13/00* (2013.01); *B08B 2209/027* (2013.01)

(56) References Cited

U.S. PATENT DOCUMENTS

| | | | |
|---|---|---|---|
| 7,918,788 | B2 | 4/2011 | Lin et al. |
| 2001/0032494 | A1 | 10/2001 | Greszler |
| 2006/0224042 | A1 | 10/2006 | Jackson et al. |
| 2006/0252991 | A1 | 11/2006 | Kubach |
| 2007/0238923 | A1 | 10/2007 | Kubach |
| 2009/0287201 | A1 | 11/2009 | Lalonde et al. |
| 2017/0020367 | A1 | 1/2017 | Tomita |
| 2018/0271356 | A1 | 9/2018 | Antonioli |
| 2019/0191981 | A1 | 6/2019 | Thate et al. |

FOREIGN PATENT DOCUMENTS

| | | | | | |
|---|---|---|---|---|---|
| JP | | 2007125385 A | * | 5/2007 | ............. A61B 1/123 |
| WO | WO-2016189985 A1 | * | 12/2016 | ............... A61B 1/12 |

OTHER PUBLICATIONS

JP2007125385 translation (Year: 2007).*
WO2016189985 translation (Year: 2016).*
International Search Report and Written Opinion dated Sep. 3, 2018 issued in PCT/EP2018/064670.
German Office Action dated Mar. 22, 2018 issued in DE 10 2017 114 816.7.
US Office Action dated Mar. 2, 2022 received in U.S. Appl. No. 16/628,334.
US Office Action dated Dec. 9, 2022 received in U.S. Appl. No. 16/628,334.

* cited by examiner

METHOD FOR RECONDITIONING AN ENDOSCOPE IN A RECONDITIONING APPARATUS, AND RECONDITIONING APPARATUS

CROSS-REFERENCE TO RELATED APPLICATION

The present application is a Divisional Application of U.S. application Ser. No. 16/628,334 filed on Jan. 3, 2020, which is based upon and claims the benefit of priority from PCT/EP2018/064670—filed on Jun. 4, 2018, which claims benefit to DE 10 2017 114 816.7 filed on Jul. 3, 2017, the entire contents of each of which are incorporated herein by reference.

BACKGROUND

Field

The present disclosure relates to a method for reconditioning an endoscope in a reconditioning apparatus, said method having the steps of: connecting an interior of the endoscope to a leakage tester of the reconditioning apparatus, supplying the interior with a fluid at a predefined pressure, and carrying out a reconditioning process using rinsing liquid, wherein the pressure in the interior of the endoscope is monitored during the reconditioning process, and wherein the endoscope to be reconditioned is identified as defective if the profile of the pressure deviates from a predefinable or predefined pressure profile. The present disclosure additionally relates to a reconditioning apparatus for endoscopes.

Prior Art

Endoscopes have been used for many years now, especially in medicine, to examine and/or treat regions that are difficult to access in the body of a human or animal patient. For this purpose, endoscopes in most cases have an elongate shaft, at the distal end of which there is an objective through which a region of interest in the body of the patient can be viewed. At the proximal end of the shaft there is in most cases a main body which serves for manipulating the endoscope.

Endoscopes often have inner channels through which fluids can be conveyed to the distal end of the endoscope, in order to be released there. Alternatively, by way of corresponding channels, fluids can also be taken in at the distal end of the endoscope and aspirated in the direction of the main body. Furthermore, treatment instruments can be advanced through corresponding channels of the endoscope to the distal end, in order to perform an intervention at the region of interest in the body.

Endoscopes are very difficult and therefore expensive to produce. In order to keep costs down, endoscopes are therefore used multiple times. This necessitates thorough reconditioning of the endoscopes between two uses, in order to prevent transmission of diseases.

A distinction is made in principle between rigid and flexible endoscopes. Rigid endoscopes generally have a shaft and channels made of a medical-grade stainless steel and are largely or completely sealed off by means of cohesively bonded connections. Therefore, rigid endoscopes can be reconditioned without any problem.

By contrast, flexible endoscopes, at least in the region of the shaft, have a sheath and channels made of a flexible plastic. If this plastic becomes damaged, contaminating material can enter the interior of the endoscope during use, which material is difficult to effectively remove during the reconditioning. Likewise, during the reconditioning, which in most cases takes place using various rinsing liquids, it is possible for rinsing liquid to penetrate the interior of the endoscope and cause permanent damage to the latter.

Prior to the reconditioning of flexible endoscopes, it is therefore essential to check whether the sheath of the endoscope is intact. For this purpose, modern reconditioning apparatuses have a leakage tester.

The leakage tester functions according to the principle by which a fluid, in most cases air, is supplied to the interior of the endoscope via a specially provided port. The pressure profile in the interior is then measured, and the pressure profile is used to conclude whether the endoscope is sufficiently leaktight.

The pressure in the interior of the endoscope is in most cases maintained during the actual reconditioning, such that no rinsing liquid can penetrate the interior, even through unobserved microscopic defects in the plastic sheath.

In the reconditioning of flexible endoscopes, different rinsing liquids are used in succession at different temperatures. The temperature of the fluid in the interior of the endoscope also increases. In order to avoid damage to the plastic sheath of the endoscope as a result of the internal pressure being too high, the pressure is monitored during the reconditioning process. If the pressure rises above an upper limit value, some of the fluid is drained off in order to reduce the pressure.

If the temperature drops again, then the pressure in the interior of the endoscope also drops. As soon as the pressure drops below a lower limit value, additional fluid is again conveyed into the interior in order to bring the pressure to the setpoint value again.

The leakage tester monitors how long it takes for the setpoint value of the pressure to be reached again after a drop in pressure. If this takes too long, the endoscope is identified as defective and the reconditioning process is discontinued.

A drop in pressure in the interior of the endoscope can likewise be caused by a loss of leaktightness of the plastic sheath. The leakage tester therefore likewise monitors how often the pressure drops below the lower limit value. If this happens too often, the endoscope is likewise identified as defective.

The limit values at which the leakage tester identifies an endoscope as defective generally have a certain tolerance, and so identification errors should be avoided. However, on account of this tolerance, the ability of the leak tester to detect very slight losses of leaktightness is limited.

SUMMARY

It is therefore an object to make available a method for reconditioning endoscopes in a reconditioning apparatus, and also a corresponding reconditioning apparatus which is improved in respect of one or more of the problems described.

According to one embodiment, such object can be achieved by a method for reconditioning an endoscope in a reconditioning apparatus, said method having the steps of: connecting an interior of the endoscope to a leakage tester of the reconditioning apparatus, supplying the interior with a fluid at a predefined pressure, and carrying out a reconditioning process using rinsing liquid, wherein the pressure in the interior of the endoscope is monitored during the reconditioning process, and wherein the endoscope to be reconditioned is identified as defective if the profile of the pressure deviates from a predefined pressure profile, wherein the predefined pressure profile is determined according to process parameters of the reconditioning process.

By the described measure, fluctuations of the pressure profile that are caused by process parameters of the reconditioning process can be differentiated from those fluctuations of the pressure profile that are caused by loss of leaktightness of the endoscope. In this way, the ability of the leakage tester to identify loss of leaktightness of the endoscope can be improved.

In the method, fluid can be drained from the interior of the endoscope if the pressure exceeds an upper limit value. This can prevent the endoscope from being damaged by too high a pressure in its interior, for example if the pressure rises through an increase in temperature.

Additionally or alternatively, additional fluid can be introduced into the interior of the endoscope if the pressure drops below a lower limit value. It is thus ensured that a sufficient pressure is maintained in the interior of the endoscope even after a drop in pressure, for example after a drop in the temperature. In this way, it is possible to prevent rinsing liquid from entering the interior of the endoscope through microscopic losses of leaktightness in the endoscope.

In an embodiment of the method, the predefined pressure profile is distinguished by a time that should be the maximum needed to bring the pressure to a setpoint value after the pressure has dropped below the lower limit value. If additional fluid is introduced through the leakage tester into the interior of the endoscope, then the pressure must rise accordingly and reach a setpoint value within a predefined time. However, if the pressure does not reach the setpoint value within a predefined time, this indicates a loss of leaktightness of the endoscope.

According to a further embodiment of the method, the predefined pressure profile is distinguished by a maximum frequency at which the pressure is allowed to drop below the lower limit value. For technical reasons, a slow drop in pressure caused by system-inherent loss of leaktightness is not completely avoidable. With a known operating time of a reconditioning process and an admissible pressure drop rate, it is possible to determine how often the pressure may drop below the lower limit value during the reconditioning process. If the pressure frequently drops below the lower limit value during the reconditioning process, this is an indicator of inadmissible loss of leaktightness of the endoscope.

In a variation of the method, the process parameters can comprise the temperature of the rinsing liquid. During the reconditioning process, the rinsing liquid contacts and flows through the endoscope and thereby influences the temperature of the fluid in the interior of the endoscope, hence also the pressure thereof. By taking the temperature of the rinsing liquid into consideration in the determination of an admissible pressure profile, temperature-induced pressure fluctuations can be better distinguished from pressure fluctuations caused by loss of leaktightness.

The process parameters can comprise the profile of the temperature of the rinsing liquid. In this way, the sensitivity in the detection of loss of leaktightness can be further enhanced.

In the method, the temperature or the temperature profile of the rinsing liquid can be determined by means of sensors provided in the reconditioning apparatus. Such sensors are present anyway in the reconditioning apparatus in order to control the temperature of the rinsing liquid according to the requirements of the reconditioning process.

Alternatively or additionally, the temperature or the temperature profile of the rinsing liquid can be determined on the basis of a setpoint temperature or setpoint temperature profile stored in a controller of the reconditioning apparatus. In this way, the data communication required during the reconditioning process, between the controller and the leakage tester, can be reduced, since the admissible pressure profile can already be determined at the start of the reconditioning process without requiring access to real-time data from sensors.

In the method, several reconditioning programs for different endoscope types and/or different kinds and/or extents of soiling are stored in the controller of the reconditioning apparatus, a reconditioning program is selected at the start of the reconditioning of the endoscope, and a temperature profile, stored for the selected reconditioning program, of the rinsing liquid is used to establish the predefined or predefinable pressure profile. In this way, the detection of loss of leaktightness can take place optimally on an individual basis for each reconditioning process that is to be carried out.

According to a further embodiment, such object can be achieved by a reconditioning apparatus for endoscopes, having a reconditioning assembly, a controller and a leakage tester, which reconditioning apparatus is configured to carry out a method according to the above description. As regards the effects and advantages thereby achieved, explicit reference is made to what has been set out above.

BRIEF DESCRIPTION OF THE DRAWINGS

The embodiments are explained in more detail below with reference to a number of exemplary figures, in which.

DETAILED DESCRIPTION

Figure 1:
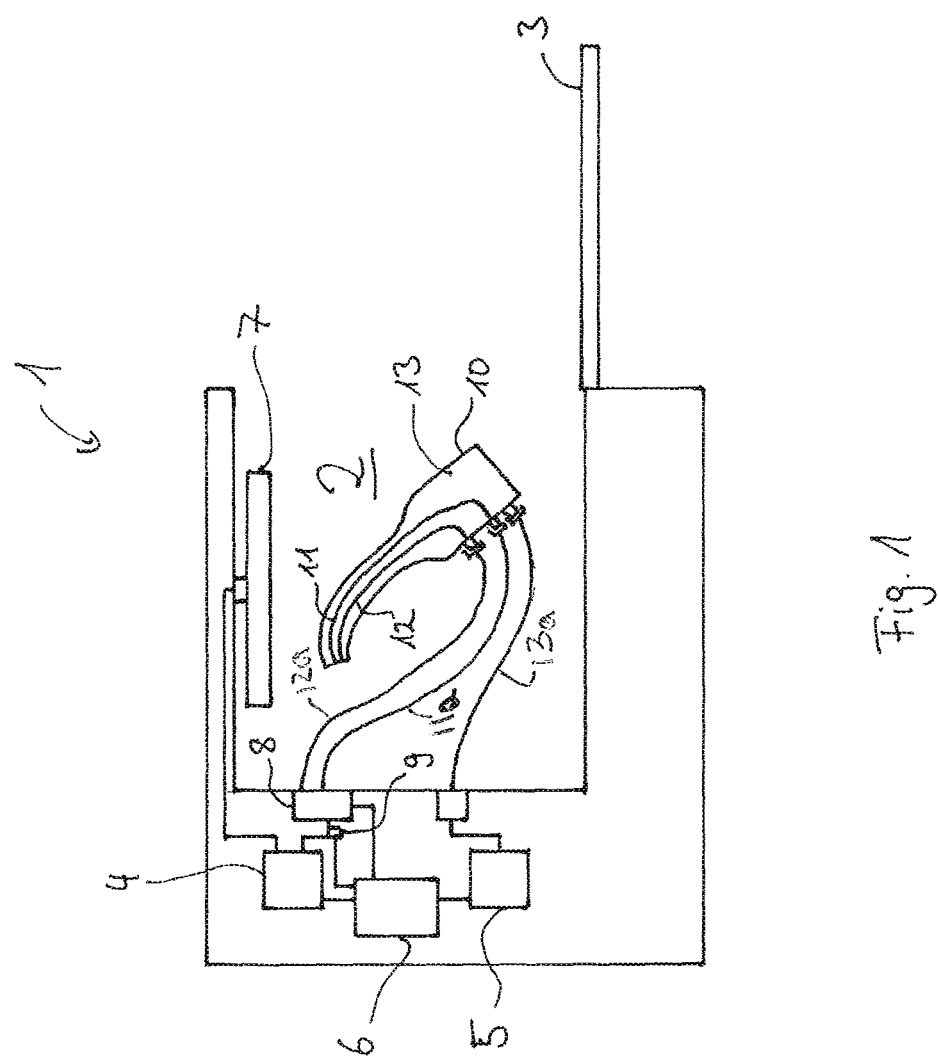
FIG. 1 illustrates a structure of a reconditioning apparatus for endoscopes.

A structure of a reconditioning apparatus for endoscopes is shown in FIG. 1. The reconditioning apparatus 1 has a rinsing chamber 2 which can be closed by a door 3. The reconditioning apparatus 1 moreover comprises a rinsing device 4, a leakage tester 5 and a controller 6.

The rinsing device 4 is connected to a spray arm 7 in the rinsing chamber 2. Furthermore, the rinsing device 4 is connected to a rinse distributor 8. A temperature sensor 9 is arranged on a line leading from the rinsing device 4 to the rinse distributor 8. Rinsing device 4, spray arm 7 and rinse distributor 8 form a reconditioning assembly of the reconditioning apparatus 1.

An endoscope 10 to be reconditioned is arranged in the rinsing chamber 2. The endoscope has two inner channels 11, 12 and also an interior 13. For the reconditioning, the channels 11, 12 of the endoscope 10 are connected to the rinse distributor 8 via hoses 11a, 12a. The interior 13 of the endoscope 10 is connected to the leakage tester 5 via a further hose 13a.

Figure 2:
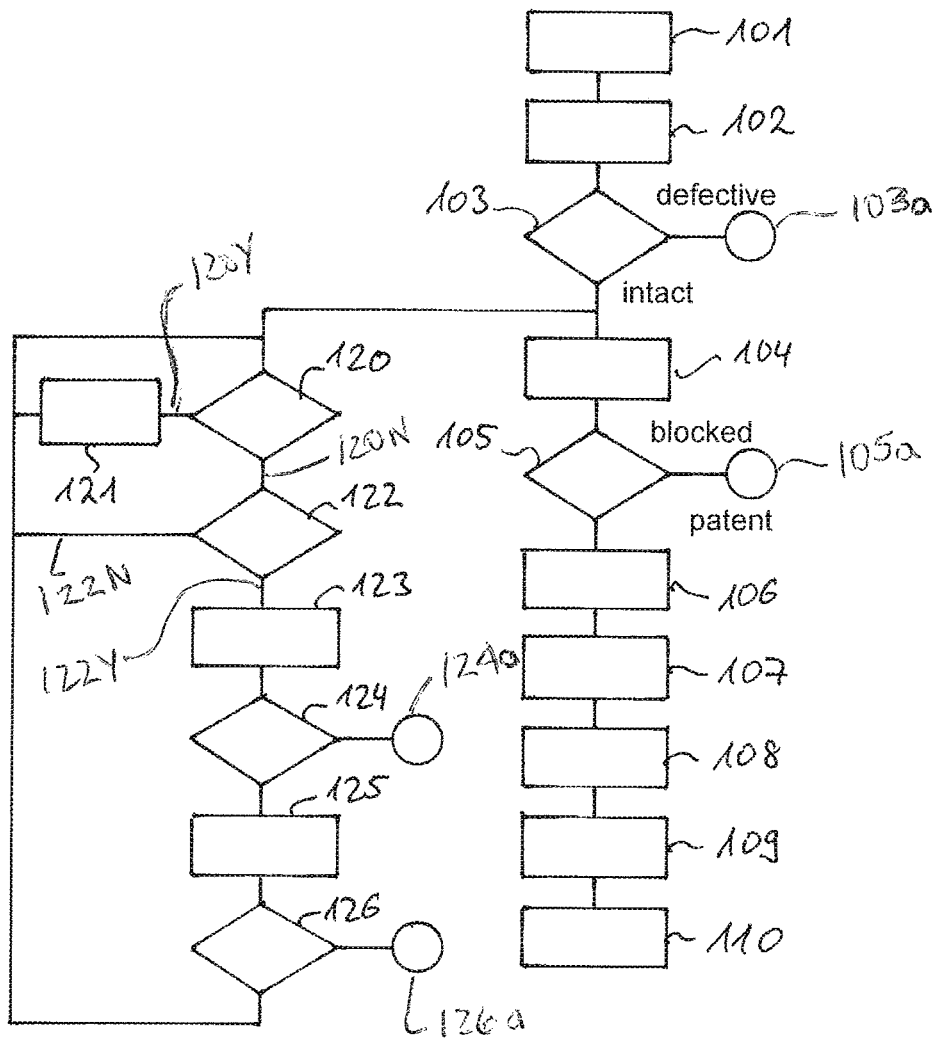
FIG. 2 illustrates a sequence of a reconditioning process.

FIG. 2 shows the sequence of a process of reconditioning of the endoscope 10.

In a step 101, the endoscope 10 is connected to the rinse distributor 8 and to the leakage tester 5, and the door 3 is then closed.

In a next step 102, an initial leakage test of the endoscope 10 is carried out. For this purpose, the interior 13 of the endoscope 10 is filled with a fluid, for example air, through the leakage tester 5 until a predefined setpoint pressure is reached. The pressure is then monitored for a predefined time. If the setpoint pressure is not reached in a predefined time, or if the pressure then drops below a lower limit value, the endoscope 10 is identified as defective, and the process is discontinued (branch 103a).

Next, in a step 104, the patency of the channels 11, 12 is checked. For this purpose, the controller 6 activates the rinsing device 4 in order to pump rinsing liquid, for example water, to the rinse distributor 8. The rinse distributor 8 is provided with valves (not shown) which are driven by the controller 6 such that the rinsing liquid is passed through the channels 11, 12 successively. The rinsing device 4 checks the flow through the channels 11, 12. If the flow through the channels 11, 12 is insufficient, the endoscope 10 is identified as being blocked, and the process is discontinued (branch 105a).

If the channels 11, 12 of the endoscope 10 are unobstructed, the endoscope 10 is treated in a step 106 with cleaning agent. For this purpose, the rinsing device 4 pumps cleaning agent to the rinse distributor 8 and to the spray arm 7, such that cleaning agent flows through and wets the interior of the channels 11, 12 and the exterior of the endoscope 10.

In a next step 107, residues of the cleaning agent are removed, which is done by rinsing the channels 11, 12 from the inside, and the endoscope 10 from the outside, with water.

In a subsequent process step 108, the channels 11, 12 of the endoscope 10 are treated from the inside, and the endoscope 10 from the outside, by a disinfectant.

In a step 109, residues of the disinfectant are in turn rinsed out with water. In a final step 110, the endoscope 10 is dried.

In parallel with the process steps 104 to 110, a continuous monitoring of the pressure in the interior 13 of the endoscope 10 runs as a loop. For this purpose, it is first of all ascertained whether the pressure has exceeded an admissible upper limit (branch 120Y). In this case, fluid is drained off in step 121 until the pressure corresponds again to the setpoint value. Thereafter, the loop begins anew to step 120.

If the pressure is not too high (branch 120N), a check is made to ascertain whether the pressure has dropped below a lower limit value at step 122. If this is not the case (branch 122N), the loop starts anew at step 120. By contrast, if the pressure has dropped below the lower limit value (Branch 122Y), then in step 123 a counter is increased which indicates the number of drops in pressure. When this counter at step 124 reaches a predefined maximum value, the endoscope 10 is identified as defective and the reconditioning process is discontinued (branch 124a).

If the maximum value is not yet reached, then in step 125 fluid is again introduced into the interior 13 of the endoscope 10 in order to increase the pressure once more to the setpoint pressure. If the setpoint pressure is not reached within a predefined time, the endoscope 10 is likewise identified as defective, and the reconditioning process is discontinued (branch 126a). Otherwise, the loop starts anew.

Figure 3:
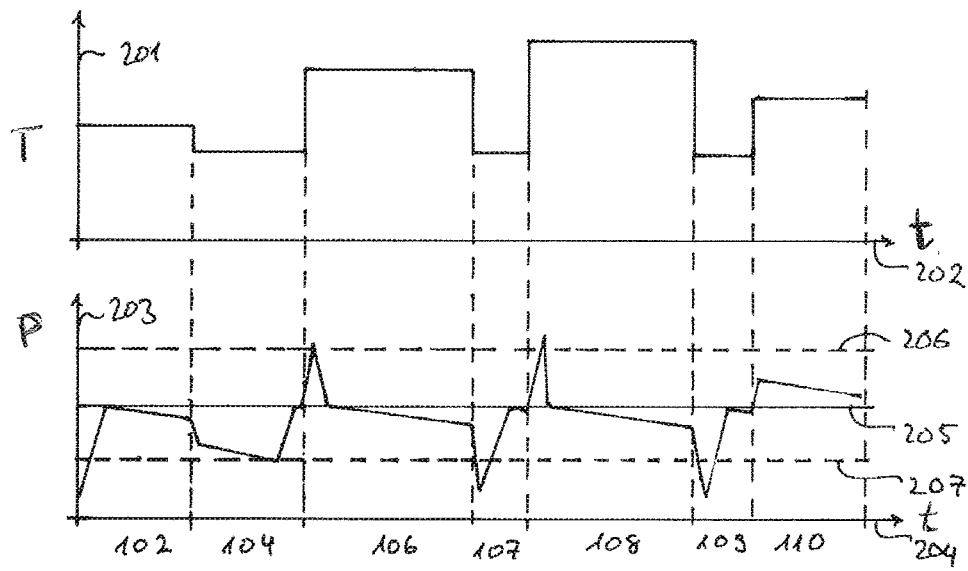
FIG. 3 illustrates a graphical representation of a profile of the temperature and of the internal pressure during a process of reconditioning an intact endoscope.

FIG. 3 shows an exemplary profile of a temperature T of the endoscope 10 and of the pressure P in the interior 13 of the endoscope, which is reconditioned by the process shown in FIG. 2.

In the upper diagram, the temperature T of the endoscope 10 is shown in an arbitrary scale on the ordinate 201. The time t is shown in an arbitrary scale on the abscissa 202.

A direct measurement of the temperature of the endoscope 10 during the reconditioning process is difficult, since sensors are not generally provided for this purpose in the endoscope 10. However, the temperature corresponds very precisely to the temperature of the rinsing liquid, which can be measured by the sensor 9 for example. Instead of a measurement of the temperature, it is also possible to use an instantaneous temperature setpoint value that is stored in the controller 6.

In the lower diagram, the pressure P in the interior 13 of the endoscope is shown on the ordinate 203, again on an arbitrary scale. The pressure is determined here by sensors in the leakage tester 5. A solid horizontal line 205 represents a setpoint pressure. Broken lines 206, 207 represent an upper and a lower limit value for the pressure.

The time t is again shown on the abscissa 204, wherein the axes 202 and 204 are at the same scale. The process steps of the reconditioning process are indicated in the diagrams by vertical lines. For greater clarity, the reference sign belonging to the respective process step from FIG. 2 is indicated again under the axis 204.

In process step 102, no rinsing agent is yet used, and the temperature therefore corresponds to the ambient temperature. The pressure initially rises from a low starting pressure to the setpoint pressure, while the leakage tester 5 pumps air into the interior 13 of the endoscope 10. After the setpoint pressure is reached, the pressure slowly falls on account of system-inherent leakage, but without yet reaching the lower limit value 207.

In step 104, water is conveyed through the channels 11, 12 of the endoscope 10, and therefore the temperature drops slightly. This results in a corresponding drop of the pressure, such that the pressure approaches the lower limit value 207 and finally reaches the latter. The leakage tester 5 registers the first drop in pressure below the lower limit value 207. However, on account of the preceding drop in temperature, the drop in pressure is not interpreted by the leakage tester 5 as a defect of the endoscope 10.

The leakage tester 5 then continues to pump air into the interior 13, such that the setpoint pressure 205 is again reached.

In the next process step 106, the endoscope is treated with warm cleaning agent, such that the temperature rises rapidly. The pressure likewise rises to the upper limit value 206, which causes the leakage tester 105 to release air from the interior 13 of the endoscope 10 until the pressure again corresponds to the setpoint pressure 205. From there, the pressure drops slowly again, but without falling below the lower limit value 207.

At the start of the process step 107, in which the endoscope 10 is treated with cold water, the temperature and pressure drop sharply, with the pressure falling below the lower limit value 207. This too is not identified by the leakage tester 5 as a defect of the endoscope 10, since the drop in pressure is associated with a drop in temperature.

The leakage tester 5 again pumps air into the interior 13 of the endoscope 10 until the setpoint pressure 205 is reached.

In step 108, the disinfection the endoscope 10 takes place, wherein the temperature is still higher than during step 106. There is again a rise in pressure, and air is released.

In step 109, the endoscope 10 is rinsed again with water, such that the temperature and the pressure drop again. The pressure likewise drops below the lower limit value 207, but the endoscope 10 is correctly interpreted as intact.

In the drying step 110, the temperature increases slightly, but this no longer has any relevant effect on the pressure.

It will be seen that, by taking into consideration the temperature or the temperature profile in the assessment of the pressure profile, an incorrect assessment of the endoscope 10 as defective can be avoided, without the lower limit value 207 for the pressure having to be set very low, or a defined number of drops in pressure below the limit value can be permitted independently of the temperature profile. In this way, the detection performance of the leakage tester 5 is improved.

Figure 4:
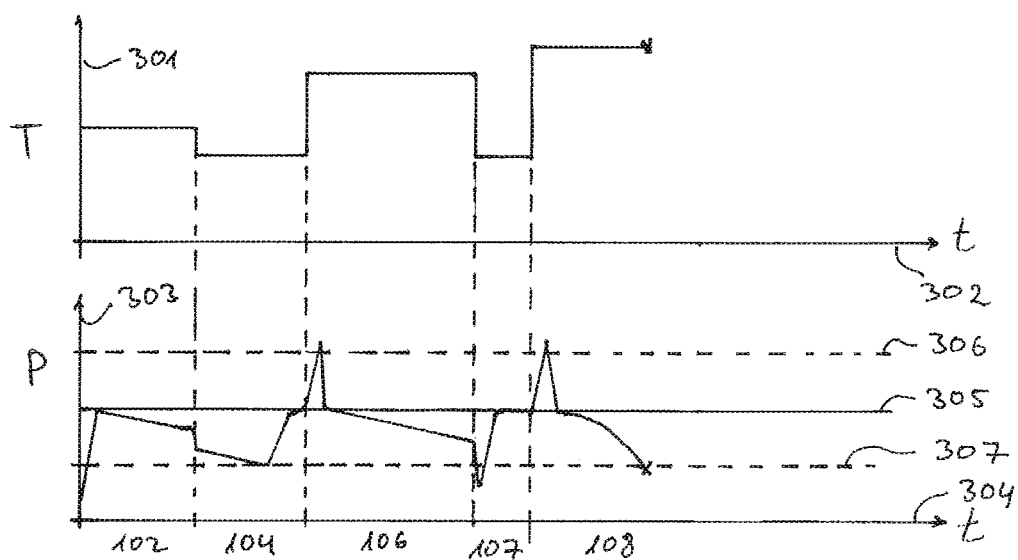
FIG. 4 illustrates a graphical representation of a profile of the temperature and of the internal pressure during a process of reconditioning a defective endoscope.

FIG. 4 shows the profile of the pressure P and of the temperature T during a reconditioning process in which a defect of the endoscope 10 occurs.

The axes and process steps correspond to those of FIG. 3. They are therefore provided with a reference sign in each case increased by 100 and are not described all over again.

In the reconditioning process shown in FIG. 4, the disinfection in process step 108 at a high temperature has the effect that the sheath of the endoscope 10 is corroded by the disinfection solution. This can occur, for example, when the endoscope 10, after a great number of uses and reconditioning processes, has reached the end of its useful life, or when one of the channels 11, 12 has been damaged by a surgical instrument during use.

Through the action of the disinfection solution, the sheath of the endoscope becomes porous and air-permeable, such that the pressure in the interior 13 of the endoscope drops below the lower limit value 307 before the end of the process step 108. Since the drop in pressure has not been preceded by a corresponding drop in temperature, the leakage tester 5 identifies the defect of the endoscope 10 and discontinues the reconditioning process.

The endoscope 10 can thus be forwarded for inspection and possibly for repair before large quantities of disinfection solution penetrate the interior 13 and damage the endoscope 10, possibly irreparably.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A reconditioning apparatus for an endoscope, the reconditioning apparatus comprising:
   a controller comprising hardware, the controller being configured to:
   supply an interior of the endoscope with a fluid at a predefined pressure;
   supply one or more channels of the endoscope and an exterior of the endoscope with a rinsing liquid to carry out a reconditioning process using the rinsing liquid;
   concurrently with the supplying of the rinsing liquid, determine a temperature and a pressure in the interior of the endoscope during the reconditioning process; and
   when the determined pressure decreases lower than a predetermined pressure:
   identify the endoscope as not defective, when the decrease in the determined pressure is preceded by a corresponding decrease in the determined temperature, and
   identify the endoscope as defective, when the decrease in the determined pressure is not preceded by a corresponding decrease in the determined temperature.

2. The reconditioning apparatus according to claim 1, wherein the controller is further configured to drain the fluid from the interior of the endoscope if the determined pressure exceeds an upper limit value.

3. The reconditioning apparatus according to claim 1, wherein the controller is further configured to introduce additional fluid into the interior of the endoscope if the determined pressure decreases below the predetermined pressure.

4. The reconditioning apparatus according to claim 3, wherein the predetermined pressure is a predefined pressure profile, the predefined pressure profile is distinguished by one of a time that is a maximum needed to bring the pressure to a setpoint value after the pressure has dropped below the predetermined pressure or a maximum frequency at which the pressure is allowed to drop below the predetermined pressure.

5. The reconditioning apparatus according to claim 1, wherein the controller is further configured to determine the temperature of the rinsing liquid based on a received output from a sensor indicating the temperature of the rinsing liquid.

6. The reconditioning apparatus according to claim 1, wherein the controller is further configured to determine the temperature of the rinsing liquid based on a stored setpoint temperature or a stored setpoint temperature profile.

7. The reconditioning apparatus according to claim 1, wherein the controller is further configured to:
   store a plurality of reconditioning programs for one or more of different types of endoscopes, different kinds of soiling encountered during the reconditioning process and different amounts of soiling encountered during the reconditioning process;
   select a reconditioning program from the plurality of reconditioning programs when starting the reconditioning process of the endoscope; and
   use a profile of the temperature of the rinsing liquid, stored for the selected reconditioning program, to establish the predetermined pressure.

8. The reconditioning apparatus according to claim 1, further comprising a rinsing chamber for accommodating the endoscope.

9. The reconditioning apparatus according to claim 8, further comprising a spray arm configured to spray the exterior of the endoscope in the rinsing chamber with the rinsing liquid.

10. The reconditioning apparatus according to claim 9, further comprising a rinsing device configured to pump the rinsing liquid to the spray arm.

11. The reconditioning apparatus according to claim 8, further comprising:

a rinse distributor configured to supply the one or more channels of the endoscope in the rinsing chamber with the rinsing liquid, and
a hose corresponding to each of the one or more channels for connecting the rinse distributor to each of the one or more channels.

12. The reconditioning apparatus according to claim 11, further comprising a rinsing device configured to pump the rinsing liquid through the rinse distributor and each corresponding hose to the exterior of the endoscope and to the one or more channels.

13. The reconditioning apparatus according to claim 1, further comprising:
a leakage tester configured to pump fluid into the interior of the endoscope and to determine the temperature and the pressure in the interior of the endoscope during the reconditioning process; and
a hose configured to connect the leakage tester to the interior of the endoscope.

14. A reconditioning apparatus for an endoscope, the reconditioning apparatus comprising:
a rinsing chamber for accommodating the endoscope;
a spray arm configured to spray the exterior of the endoscope in the rinsing chamber with the rinsing liquid;
a rinse distributor configured to supply one or more channels of the endoscope in the rinsing chamber with the rinsing liquid;
a first hose corresponding to each of the one or more channels for connecting the rinse distributor to each of the one or more channels;
a rinsing device configured to pump the rinsing liquid to the spray arm and to to pump the rinsing liquid through the rinse distributor and each corresponding hose to the exterior of the endoscope and to the one or more channels;
a leakage tester configured to pump fluid into an interior of the endoscope and to determine the temperature and the pressure in the interior of the endoscope during the reconditioning process;
a second hose configured to connect the leakage tester to the interior of the endoscope; and
a controller comprising hardware, the controller being configured to:
control the leakage tester to supply an interior of the endoscope with a fluid at a predefined pressure;
control the rinsing device to supply the one or more channels of the endoscope and an exterior of the endoscope with a rinsing liquid to carry out a reconditioning process using the rinsing liquid;
concurrently with the supplying of the rinsing liquid, determine a temperature and a pressure in the interior of the endoscope during the reconditioning process; and
when the determined pressure decreases lower than a predetermined pressure:
identify the endoscope as not defective, when the decrease in the determined pressure is preceded by a corresponding decrease in the determined temperature, and
identify the endoscope as defective, when the decrease in the determined pressure is not preceded by a corresponding decrease in the determined temperature.

15. The reconditioning apparatus according to claim 14, wherein the controller is further configured to control the leakage tester to drain the fluid from the interior of the endoscope if the determined pressure exceeds an upper limit value.

16. The reconditioning apparatus according to claim 14, wherein the controller is further configured to control the leakage tester to introduce additional fluid into the interior of the endoscope if the determined pressure decreases below the predetermined pressure.

17. The reconditioning apparatus according to claim 14, further comprising a sensor, wherein the controller is further configured to determine the temperature of the rinsing liquid based on a received output from the sensor indicating the temperature of the rinsing liquid.

18. The reconditioning apparatus according to claim 14, further comprising a memory, wherein the controller is further configured to determine the temperature of the rinsing liquid based on a setpoint temperature stored in the memory or a setpoint temperature profile stored in the memory.

19. The reconditioning apparatus according to claim 14, further comprising a memory storing a plurality of reconditioning programs for one or more of different types of endoscopes, different kinds of soiling encountered during the reconditioning process and different amounts of soiling encountered during the reconditioning process,
wherein the controller is further configured to:
recall, from the memory, the plurality of reconditioning programs for one or more of different types of endoscopes, different kinds of soiling encountered during the reconditioning process and different amounts of soiling encountered during the reconditioning process;
select a reconditioning program from the plurality of reconditioning programs when starting the reconditioning process of the endoscope; and
use a profile of the temperature of the rinsing liquid, stored for the selected reconditioning program, to establish the predetermined pressure.

20. Non-transitory computer-readable storage medium storing instructions that cause a computer to at least perform:
supplying an interior of an endoscope with a fluid at a predefined pressure;
supplying one or more channels of the endoscope and an exterior of the endoscope with a rinsing liquid to carry out a reconditioning process using the rinsing liquid;
concurrently with the supplying of the rinsing liquid, determining a temperature and a pressure in the interior of the endoscope during the reconditioning process; and
when the determined pressure decreases lower than a predetermined pressure:
identifying the endoscope as not defective, when the decrease in the determined pressure is preceded by a corresponding decrease in the determined temperature, and
identifying the endoscope as defective, when the decrease in the determined pressure is not preceded by a corresponding decrease in the determined temperature.

* * * * *